United States Patent [19]

Chang et al.

[11] Patent Number: 4,755,217
[45] Date of Patent: Jul. 5, 1988

[54] TRIAZINEDIONE HERBICIDES

[75] Inventors: Jun H. Chang, Princeton Junction; John W. Lyga, Basking Ridge, both of N.J.

[73] Assignee: FMC Corporation, Philadelphia, Pa.

[21] Appl. No.: 81,639

[22] Filed: Jul. 31, 1987

Related U.S. Application Data

[63] Continuation-in-part of Ser. No. 3,448, Jan. 15, 1987, abandoned.

[51] Int. Cl.$^4$ .................. A01N 43/84; C07D 413/04
[52] U.S. Cl. ........................................ 71/93; 71/88; 544/105
[58] Field of Search ............................. 544/105; 71/93

[56] References Cited

U.S. PATENT DOCUMENTS

| | | | |
|---|---|---|---|
| 4,139,364 | 2/1979 | Wolf | 544/105 X |
| 4,619,687 | 10/1986 | Haga et al. | 71/92 |
| 4,640,707 | 2/1987 | Nagano et al. | 544/105 X |

FOREIGN PATENT DOCUMENTS

| | | |
|---|---|---|
| 0170191 | 2/1986 | European Pat. Off. |
| 8600072 | 1/1986 | PCT Int'l Appl. |

*Primary Examiner*—Richard L. Raymond

*Attorney, Agent, or Firm*—Robert M. Kennedy; H. Robinson Ertelt; Abner Sheffer

[57] ABSTRACT

Herbicidal compounds of the formula

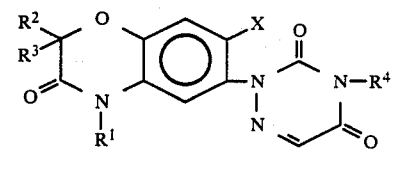

or

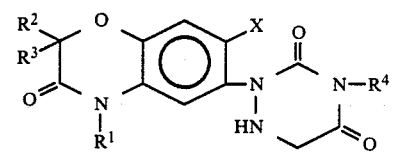

in which $R^1$ is H, alkyl, alkenyl, alkynyl, haloalkyl, haloalkenyl, haloalkynyl, alkoxyalkyl, alkoxyalkoxyalkyl, alkylsulfonyl, aralkyl, alkylthioalkyl, hydroxy or alkoxy;

$R^2$ and $R^3$ are independently H or alkyl;

X is H, Cl or F;

$R^4$ is alkyl, haloalkyl, alkenyl or alklynyl.

10 Claims, No Drawings

TRIAZINEDIONE HERBICIDES

This application is a continuation-in-part, of application Ser. No. 003.448, filed 1-15-87, now abandoned, This invention relates to 1,2,4-triazine-3,5(2H,4H)-diones and dihydro-1,2,4-triazine-3,5-diones of the following formulas I and II and their use as herbicides:

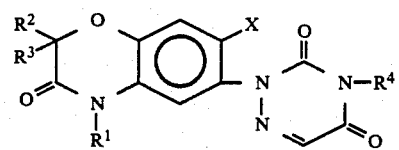

Formula I

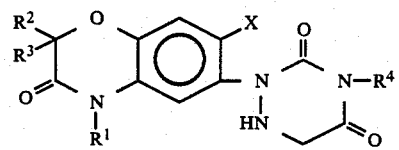

Formula II in which $R^1$ is,

H:
alkyl, e.g. methyl, ethyl or propyl:
alkenyl, e.g. allyl or methyallyl;
alkynyl, e.g. propynyl or methylpropynyl;
haloalkyl, e.g. 3-chloropropyl;
haloalkenyl, e.g. 2-chloropropenyl;
haloalkynyl, e.g. 3-bromopropynyl;
alkoxyalkyl, e.g. methoxymethyl or ethoxymethyl;
alkoxyalkoxyalkyl, e.g. ethoxymethoxymethyl;
alkylsulfonyl, e.g. methylsulfonyl or ethylsulfonyl;
cycloalkyl, e.g., cyclopropylmethyl or cyclopropyl;
aralkyl, e.g. benzyl;
alkylthioalkyl, e.g. methylthiomethyl;
hydroxy; or alkoxy, e.g. methoxy or ethoxy.

$R^2$ and $R^3$ are, independently H or alkyl, e.g. methyl, preferably H. X is H, Cl or F, preferably F.

$R^4$ is alkyl (e.g. methyl or ethyl), haloalkyl (e.g. fluoroalkyl such as $CH_2F$, $CH_2CH_2F$ or $CH_2(CH_2)_2F$), alkenyl (e.g. allyl), alkynyl (e.g. propynyl).

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 carbon atoms.

The compounds of this invention may be prepared by the use of steps generally described in the literature or in the following Examples or by methods analogous or similar thereto and within the skill of the art. In Examples below, there is formed a 2-aryl-1,2,4-triazine-3,5(2H,4H)-dione from an aniline in known manner (such as in the manner taught in published International Application No. WO 86/0072 published Jan. 3, 1986). The aryltriazinedione is treated to introduce a carboalkoxymethoxy or similar group at the 4-position of the benzene ring and a nitro group at the 5-position to form a compound of the formula

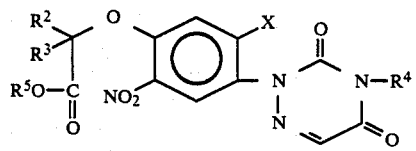

where $OR^5$ is alkoxy or, similar group which can be split out in the next step. Specifically, in Example 1, 2,4-difluoroaniline is converted to a compound of the formula

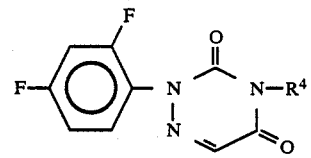

which is then nitrated to give a compound of the formula

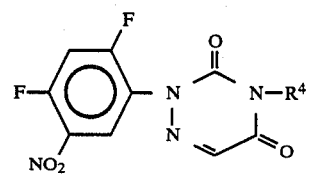

after which the carboalkoxymethoxy group was introduced. Then, in known manner (J. Am. Chem. Soc., 81, 94 (1959)) by treatment with iron in an acidified solvent, e.g. at an elevated temperature such as 60–150° C., reduction of the nitro group to an amino group, followed by ring closure between said 4- and 5-positions is effected, forming a compound of the formula,

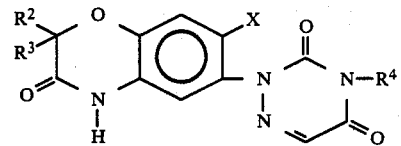

After this an $R^1$ group is introduced, as by reaction with $R^1X^1$ (where $X^1$ is a leaving group such as a halogen) to form the final compound.

To produce compounds in which $R^1$ is hydroxy or alkoxy the reduction and ring closure step may be effected by using a milder reducing agent (such as hydrazine in the presence of rhodium on carbon) to form, during the reaction, an intermediate having a —NHOH group (instead of an —NH$_2$ group) at the 5-position of the benzene ring so that on cyclization there is formed a compound having the formula

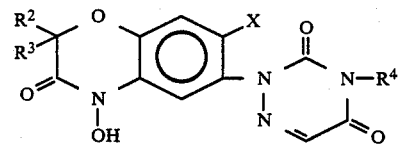

after which that compound is treated with an appropriate alkyl halide (e.g. methyl iodide in the presence of NaH).

To produce compounds in which $R^1$ is haloalkynyl the compound in which $R^1$ is alkynyl may be reacted with the halogen (e.g. iodine or bromine) in the presence of a base (e.g. NaOH or KOH); also a catalyst such as benzyltriethylammonium bromide or chloride or tetrabutylammonium bromide may be present.

The compounds of Formula II above which are dihydro-1,2,4-triazine-3,5-diones, may be prepared by the same process except for the additional step of selectively reducing corresponding 1,2,4-triazine-3,5(2H,4H)-dione intermediate (or final product), e.g. by using powdered zinc in an aqueous acid medium (e.g sulfuric acid or more preferably acetic acid) according to the general method set forth in Coll. Czech. Chem. Comm. 39, 3760 (1974). Other methods and descriptions of the hydrogenated compounds are found in Neunhoeffer and Wiley "Chemistry of 1,2,3-Triazines and 1,2,4-Triazines, Tetrazines, and Pentazines" pub. 1978 by Interscience, pages 613–618 and 1006–1033.

The following Examples are given to illustrate this invention further. In this application all parts are by weight unless otherwise indicated. In the Examples, the term "concentrated", referring to a procedure in the process, relates to evaporating under reduced pressure in conventional manner to remove volatiles such as solvent. Also, in the Examples, the mixtures are stirred in conventional fashion and the reaction is carried out in inert atmosphere when appropriate (e.g. in the reaction involving sodium hydride).

EXAMPLE 1

Step A 47.5 g of 2,4-difluoroaniline (0.368 mol) was added to a suspension of 100 g malonyldiurethane (0.406 mol) in 3 liters of water containing 100 g sodium acetate and 50 ml of concentrated HCl. The resulting mixture was cooled to about 10° C. and a solution of 24 g of sodium nitrite in 50 ml of water was added dropwise over a period of about 30 minutes at such a rate as to minimize gas evolution and avoid undue foaming. After this the mixture was stirred at about 5° C. for 1 hour and then slowly warmed to room temperature and then filtered. The resulting solid was washed with water and then partitioned between ethyl acetate and water. The ethyl acetate solution was dried over magnesium sulfate, filtered hot, and the solution was then concentrated to yield about 105 g of a creamy solid, which was largely N,N'-carboethoxy-2-ketomalonodiamide 2,4-difluorophenylhydrazone.

Step B

All of the crude solid resulting from the previous step was dissolved in 1 liter of hot tetrahydrofurane and then mixed with 900 ml of a 10% aqueous solution of KOH, forming a thick suspension which was then mixed with 1 liter of ethanol and warmed to form a solution, which was then stirred for 1 ½ hours and worked up as follows 1 liter of the solution was diluted with 1 liter of water and washed with 500 ml of ethyl acetate (which removed any unreacted difluoroaniline). The water layer was acidified (with concentrated HCl) and extracted with two 500 ml portions of ethyl acetate.

The remainder of the KOH reaction mixture was worked up in the same way. The resulting ethyl acetate extract was washed with saturated aqueous NaCl, then dried over magnesium sulfate, treated with charcoal and concentrated, yielding 43 g of a yellow solid, 2-(2,4-difluorophenyl)-6-carboxy-1,2,4-triazine-3,5(2H,4H)-dione.

Step C

All 43 g of the solid produced in Step B was suspended in 100 ml of mercaptoacetic acid and heated to about 165° C. Rapid evolution of carbon dioxide commenced at about 160° C. After two hours at the elevated temperature the mixture was poured into ice water and extracted with ethyl acetate. The resulting extract was washed with dilute aqueous NaHCO$_3$, then with saturated aqueous NaCl, then dried over MgSO$_4$ and treated with charcoal, then concentrated, yielding 23 g of a yellow solid, 2-[2,4-difluorophenyl]-1,2,4-triazine-3,5(2H,4H)-dione.

Step D 22.5 g of the 2-[2,4-difluorophenyl]-1,2,4-triazine-3,5(2H,4H)-dione (0.1 mol) in 100 ml of N,N-dimethylformamide (DMF) was added to a cold suspension of 0.11 mol of NaH in 200 ml of DMF and the resulting mixture was stirred at about room temperature for 30 minutes, then cooled externally to bring its temperature to about 20° C. while 15.6 g of methyl iodide in 50 ml DMF were added. The resulting reaction mixture was poured onto 2 liters of ice water and extracted with 1 liter of ether. The extract was washed well with 10% aqueous HCl and then dried over MgSO$_4$ and treated with charcoal, after which it was concentrated to yield 20.8 g of an oil, 2-[2,4-difluorophenyl]-4-methyl-1,-2,4-triazine-3,5(2H,4H)-dione.

Step E

All of the oil resulting from the previous step (20.8 g) was dissolved in 100 ml of concentrated H$_2$SO$_4$ and chilled to about 5° C. on an ice bath, after which a solution of 14 ml of 70% HNO$_3$ in 10 ml of concentrated H$_2$SO$_4$ was added while keeping the temperature below 10° C. The mixture was then poured into water, extracted with ethyl acetate, and then washed successively with saturated aqueous solutions of NaHCO$_3$ and NaCl, dried over magnesium sulfate and treated with charcoal, after which it was concentrated to yield a dark foam; the latter was then chromatographed on silica gel with 7/3 (by volume) heptane/ethyl acetate to yield 15 g of a yellow oil, 2-[2,4-difluoro-5-nitrophenyl]-4-methyl-1,2,4-triazine-3,5(2H,4H)dione.

Step F 5.7 g of the oil from the previous step (0.020 mol) was dissolved in 20 ml of DMF containing 0.022 mol of NaH. This solution was warmed to 40° C. while 2.0 g of methyl hydroxyacetate dissolved in 5 ml of DMF was dripped in. After an initial temperature rise to about 90° C. the temperature was regulated to about 50° C. After about 3 hours of reaction, during which the mixture turned deep red, the mixture was poured onto a mixture of ice and aqueous concentrated HCl and filtered. The resulting solid was dissolved in ethyl acetate, washed with saturated aqueous NaCl, dried over magnesium sulfate and then concentrated to a syrup, which was then chromatographed on silica gel using 1/1 (by volume) ethyl acetate/heptane to yield a middle band of 2.0 g of a yellow foam 2-(2-fluoro-4-carbomethoxymethoxy-5-nitrophenyl)-4-methyl-1,2,4-triazine-3,5(2H,4H)-dione.

Step G 1.9 g of the product of the previous step was dissolved in 40 ml of acetic acid and added to 3 g of iron powder in 60 ml of acetic acid at 80° C. After 1 hour of reaction the mixture was poured into water and then extracted with ethyl acetate. The organic layer was dried over magnesium sulfate, treated with charcoal and then concentrated to yield 1.3 g of a white powder, 2-(7-fluoro-2H-1,4-benzoxazin-3(4H)-on-6-yl)-4-methyl-1,2,4-triazine-3,5(2H,4H)-dione.

Step H 1 g (0.00342 mol) of the powder formed in the preceding step was dissolved in 5 ml of DMF under argon and added to a suspension of 0.00377 mol of NaH in 5 ml of DMF. After evolution of hydrogen ceased (about 10 minutes) the mixture was a clear dark solution. Then a solution of 0.64 g of 1-iodopropane (0.00377 mol) in 5 ml of DMF was added. After 30 minutes the mixture was poured onto a mixture of ice, concentrated HCl and water and then extracted with ethyl acetate. The extract was washed with aqueous 10% HCl and then with saturated aqueous NaCl solution, then dried over magnesium sulfate, treated with charcoal, filtered and concentrated, yielding a product which was then recrystallized from a blend of heptane and ethyl acetate to give 0.4 g of a light yellow solid, m.p. 164–166° C., 2-(7-fluoro-4-propyl-2H-1,4-benzoxazin-3(4H)-on-6-yl)-4-methyl-1,2,4-triazine-3,5(2H,4H)-dione.

To produce compounds having other $R^1$ substituents, the appropriate halide reactant may be employed in step G above; for instance, methyl iodide (for compound 3 of Table 1 below), ethyl iodide (for compound 4), propargyl bromide (for compound 6), methoxymethylbromide (for compound 7), methylthiomethyl chloride (for compound 8), benzyl bromide (for compound 9), ethylsulfonyl chloride (for compound 10).

EXAMPLE 2

To a stirred mixture of 0.09 gram (0.0038 mole) of sodium hydride in 5 mL of DMF was added a solution of 1.0 gram (0.0034 mole) of 2-(7-fluoro-2H-1,4-benzoxazin-3(4H)-on-6-yl)-4-methyl-1,2,4-triazine-3,5(2H,4H)-dione (prepared in Step F of Example 1) in 10 ml of DMF. This mixture was stirred and heated at 50° C. for ten minutes, then was cooled to 30° C. A solution of 0.45 gram (0.0038 mole) of propargyl bromide in 2 mL of DMF was added, and the resultant mixture was stirred at 30° C. for 30 minutes. This mixture was poured into a mixture of ice, water, and hydrochloric acid, forming a precipitate. THis precipitate was collected by filtration. The filter cake was dissolved in 5 mL of glacial acetic acid. This solution was added to a stirred mixture of 1.0 gram (0.015 mole) of zinc powder in 10 mL of glacial acetic acid and 5 mL of water. The resultant mixture wad heated at 60° C. for 1.5 hour, then was cooled and partitioned between ethyl acetate and water. The organic phase was washed with an aqueous, saturated sodium bicarbonate solution. The washed organic phase was dried over anhydrous magnesium sulfate and filtered. The filtrate was evaporated under reduced pressure leaving 0.45 gram of a foam. This foam was purified by chromatography on a silica gel coated, preparatory, thin layer chromatography plate. Elution was accomplished using ethyl acetate:n-heptane (1:1), to yield 0.23 gram of 2-[7-fluoro-2H-4-(2-propynyl)-1,4-benzoxazin-3(4H)-on-6-yl]-1,6-dihydro-4-methyl-1,2,4-triazine-3,5(2H,4H)-dione as a foam.

The nmr spectrum was consistent with the proposed structure.

The herbicidal data in the following Tables 3 and 4 was obtained in the manner described in PCT published application No. WO 85/01939, previously mentioned, usually employing solutions of the herbicidal compound in 50/50 acetone/water mixtures. In those tables, the test compounds are identified by numbers which correspond to those in Table 1, "kg/ha" is kilograms per hectare, and "% C" is percent control.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable power formulations are:

| Component: | % by Wt. |
| --- | --- |
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |

| Component: | % by Wt. |
|---|---|
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 6 of the tables below has, in greenhouse testing at pre-emergence dosages as low as about 0.015 and 0.007 kg/ha, given good weed control with no damage to soybeans. For field use, where there are losses of herbicide, larger dosages (e.g. four times the dosages mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)1,3,5-triazine-2,4-diamine (atrazine), and 2-[4-chloro-6-(ethylamino)-1,3,5-triazin-2-yl]amino -2-methylpropanenitrile (cyanazine); dinitrolaniline herbicides such as 2,6-dinitro-N,N-dipropyl-4-(trifluoromethyl)benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

| Cmpd. No. | X | $R^1$ | $R^2$ | $R^3$ | $R^4$ |
|---|---|---|---|---|---|
| 1 | F | H | H | H | H |
| 2 | F | H | H | H | $CH_3$ |
| 3 | F | $CH_3$ | H | H | $CH_3$ |
| 4 | F | $C_2H_5$ | H | H | $CH_3$ |
| 5 | F | $CH_2CH_2CH_3$ | H | H | $CH_3$ |
| 6 | F | $CH_2C\equiv CH$ | H | H | $CH_3$ |
| 7 | F | $CH_2OCH_3$ | H | H | $CH_3$ |
| 8 | F | $CH_2SCH_3$ | H | H | $CH_3$ |
| 9 | F | $-CH_2$ phenyl | H | H | $CH_3$ |
| 10 | F | $SO_2C_2H_5$ | H | H | $CH_3$ |
| 11 | F | $SO_2CH_3$ | H | H | $CH_3$ |
| 13 | F | $CH_2OC_2H_5$ | H | H | $CH_3$ |
| 14 | Cl | $CH_2C\equiv CH$ | H | H | $CH_3$ |
| 15 | F | $CH_2C\equiv CH$ | H | H | $CH_2F$ |
| 16 | F | $CH_2C\equiv CH$ | H | H | $CH_2CH=CH_2$ |
| 17 | F | $CH(CH_3)_2$ | H | H | $CH_3$ |
| 18 | F | $CH_2F$ | H | H | $CH_3$ |
| 19 | F | $CH_2CH_2F$ | H | H | $CH_3$ |
| 20 | F | $CH_2CN$ | H | H | $CH_3$ |
| 21 | F | $CH_2CH_2CH_2F$ | H | H | $CH_3$ |
| 22 | F | $CH_2CH_2CN$ | H | H | $CH_3$ |
| 23 | F | $CH_2CH\equiv CH-CH_3$ | H | H | $CH_3$ |
| 24 | F | $CH(CH_3)CH_2CH_3$ | H | H | $CH_3$ |

TABLE 1-continued

| Cmpd. No. | X | $R^1$ | $R^2$ | $R^3$ | $R^4$ |
|---|---|---|---|---|---|
| 25 | F | $CH_2CH(CH_3)CH_2CH_3$ | H | H | $CH_3$ |
| 26 | F | $OCH_3$ | H | H | $CH_3$ |
| 27 | F | $OCH_2CH_3$ | H | H | $CH_3$ |
| 28 | F | $CH_2SCH_2CH_3$ | H | H | $CH_3$ |
| 29 | F | $CH_2C(CH_3)=CH_2$ | H | H | $CH_3$ |
| 30 | F | $CH_2CH_2CH(CH_3)_2$ | H | H | $CH_3$ |
| 31 | F | $CH_2(CH_2)_3CH_3$ | H | H | $CH_3$ |
| 32 | F | $SO_2CH_2CH_2CH_3$ | H | H | $CH_3$ |
| 33 | F | $CH_2C\equiv Cl$ | H | H | $CH_3$ |
| 34 | F | $SO_2CH(CH_3)_2$ | H | H | $CH_3$ |
| 35 | F | $CH_2CH=CH_2$ | H | H | $CH_3$ |
| 36 | F | $CH_2(CH_2)_2CH_3$ | H | H | $CH_3$ |
| 37 | F | $CH_2-$cyclopropyl | H | H | $CH_3$ |
| 38 | F | $CH_2C(Cl)=CHCl$ (trans) | H | H | $CH_3$ |
| 39 | F | $CH_2C(Cl)=CHCl$ (cis) | H | H | $CH_3$ |
| 40 | F | $CH_2C(Br)=CH_2$ | H | H | $CH_3$ |
| 41 | F | $CH_2C(Cl)=CH_2$ | H | H | $CH_3$ |
| 42 | F | H | $CH_3$ | H | $CH_3$ |
| 43 | F | $CH_2C\equiv CH$ | $CH_3$ | H | $CH_3$ |
| 44 | F | $CHF_2$ | H | H | $CH_3$ |
| 45 | F | $CH_2CH(CH_3)_2$ | H | H | $CH_3$ |
| 46 | H | H | H | H | $CH_3$ |
| 47 | H | $CH_2CH_2CH_3$ | H | H | $CH_3$ |
| 48 | F | cyclopropyl | H | H | $CH_3$ |

Other representative compounds are identical with compounds 1-41 and 44-48 except that $R^2$ is methyl. Still others are identical with compounds 1-48 except that the triazinedinone ring is hydrogenated.

TABLE 2

| Physical Properties | |
|---|---|
| Compound No. | Melting Point ° C. |
| 1 | above 250° C. |
| 2 | 241–243 |
| 3 | 191–194 |
| 4 | 197–200 |
| 5 | 164–166 |
| 6 | foam* |
| 7 | foam* |
| 8 | 200–202 |
| 9 | 188–190 |
| 10 | foam* |
| 17 | foam* |
| 19 | 192.5–194.5 |
| 20 | 191–192 |
| 21 | 148–150 |
| 22 | 178.5–180.5 |
| 24 | foam* |
| 31 | 120–122 |
| 35 | 149–150 |
| 36 | 147.5–148.5 |
| 37 | 148.5–149.5 |
| 38 | 169–171 |
| 39 | 151–153 |
| 40 | 138.5–140 |
| 41 | 118.5–119.5 |
| 42 | above 230 |
| 43 | oily solid |
| 44 | foam* |
| 45 | 155–156 |
| 46 | 268–270 |
| 47 | 134–135 |

For each of the compounds in Table 2 and for each of the products of the Steps of the Examples, above, the nmr was consistent with the structure described.

TABLE 3

| | Preemergence Herbicidal Activity (% Control) | | | |
|---|---|---|---|---|
| | Compound No. | | | Example |
| | 5 | 6 | 7 | 2* |
| | Rate (kg/ha) | | | |
| Species | 0.125 | 0.25 | 0.25 | 0.125 |
| Cotton | 80 | 100 | 95 | 100 |
| Soybean | 5 | 95 | 70 | 5 |
| Field Corn | 100 | 100 | 100 | 100 |
| Rice | 95 | 100 | 100 | 100 |
| Wheat | 95 | 100 | 100 | 5 |
| Morningglory | 100 | 100 | 100 | 100 |
| Wild Mustard | 100 | 100 | 100 | 100 |
| Velvetleaf | 100 | 100 | 100 | 100 |
| Barnyardgrass | 100 | 100 | 100 | 100 |
| Green Foxtail | 100 | 100 | 100 | 100 |
| Johnsongrass | 100 | 100 | 100 | 100 |

*This compound is the compound of Example 2, which is the 1,6-dihydro derivative of compound 6 in Table 1.

TABLE 4

| | Postemergence Herbicidal Activity (% Control) | | | |
|---|---|---|---|---|
| | Compound No. | | | Example |
| | 5 | 6 | 7 | 2* |
| | Rate (kg/ha) | | | |
| Species | 0.125 | 0.25 | 0.25 | 0.125 |
| Cotton | 90 | 100 | 100 | 100 |
| Soybean | 60 | 95 | 90 | 90 |
| Field Corn | 100 | 100 | 100 | 100 |
| Rice | 100 | 100 | 100 | 100 |
| Wheat | 95 | 100 | 100 | 100 |
| Morningglory | 100 | 100 | 100 | 100 |
| Wild Mustard | 100 | 100 | 100 | 100 |
| Velvetleaf | 100 | 100 | 100 | 100 |
| Barnyardgrass | 95 | 100 | 100 | 100 |
| Green Foxtail | 100 | 100 | 100 | 100 |
| Johnsongrass | 70 | 100 | 90 | 100 |

*This compound is the compound of Example 2, which is the 1,6-dihydro derivative of compound 6 in Table 1.

We claim:

1. Compound of the formula

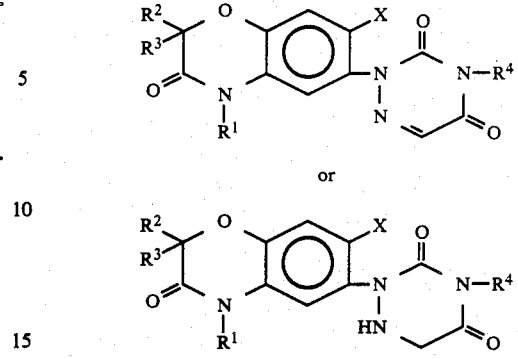

or in which $R^1$ is H, alkyl, alkenyl, alkynyl, haloalkyl, haloalkenyl, haloalkynyl, alkoxyalkyl, alkoxyalkoxyalkyl, alkyl, cyeloalkyl, aralkyl, alkylthioalkyl, hydroxy or alkoxy;

$R^2$ $R^3$ are independently H or alkyl;

X is H, Cl or F;

$R^4$ is alkyl, haloalkyl, alkenyl or alkynyl.

2. Compound of claim 1 in which $R^2$ and $R^3$ are H, X is F, $R^4$ is $CH_3$.

3. Compound of claim 2 in which $R^1$ is propynyl.

4. Compound of claim 2 in which $R^1$ is propyl.

5. Compound of claim 2 in which $R^1$ is alkyl.

6. Compound of claim 3 which is the 1,6-dihydro compound.

7. An herbicidal composition comprising an herbicidally effective amount of the compound of claim 1 in admixture with a suitable carrier.

8. A method for controlling undesired plant growth which comprises applying to the locus where control is desired an herbicid,ally effective amount of the composition of claim 7.

9. An herbicidal composition comprising an herbicidally effective amount of the compound of claim 2 in admixture with a suitable carrier.

10. A method for controlling undesired plant growth which comprises applying to the locus where control is desired an herbicidally effective among of the composition of claim 9.

* * * * *